US011602228B2

(12) United States Patent
Wang et al.

(10) Patent No.: US 11,602,228 B2
(45) Date of Patent: Mar. 14, 2023

(54) ADJUSTABLE BED WITH AROMATHERAPY SYSTEM

(71) Applicant: Nisco Co., Ltd, Jiangsu (CN)

(72) Inventors: Wei Wang, Jiangsu (CN); Jian Xie, Jiangsu (CN); Yifan Mao, Jiangsu (CN)

(73) Assignee: NISCO CO., LTD, Jiangsu (CN)

( * ) Notice: Subject to any disclaimer, the term of this patent is extended or adjusted under 35 U.S.C. 154(b) by 270 days.

(21) Appl. No.: 16/990,085

(22) Filed: Aug. 11, 2020

(65) Prior Publication Data

US 2021/0052085 A1 Feb. 25, 2021

Related U.S. Application Data

(60) Provisional application No. 62/889,145, filed on Aug. 20, 2019.

(51) Int. Cl.
*A47C 20/04* (2006.01)
*A47C 31/00* (2006.01)
*A61M 21/02* (2006.01)
*A61M 21/00* (2006.01)

(52) U.S. Cl.
CPC ............ *A47C 31/005* (2013.01); *A47C 20/04* (2013.01); *A61M 21/02* (2013.01); *A61M 2021/0016* (2013.01)

(58) Field of Classification Search
CPC ....... A47C 31/00; A47C 31/005; A47C 20/04; A61M 21/02; A61M 2021/0016
See application file for complete search history.

(56) References Cited

U.S. PATENT DOCUMENTS 5,645,578 A * 7/1997 Daffer ............... A61M 21/0094
600/27
2016/0206113 A1 * 7/2016 Rawls-Meehan .... A47C 20/048

* cited by examiner

*Primary Examiner* — Fredrick C Conley
(74) *Attorney, Agent, or Firm* — Locke Lord LLP; Tim Tingkang Xia, Esq.

(57) ABSTRACT

An adjustable bed includes a frame structure; a plurality of platforms disposed on the frame structure; and an adjustable assembly coupled with the frame structure and the plurality of platforms for operably adjusting one or more of the plurality of platforms in desired positions; and an aromatherapy system attached onto the one or more platforms for producing desired fragrance in a surrounding space of the adjustable bed so as to promote health and well-being of a user. Each aromatherapy device is configured to produce a fragrance when said aromatherapy device is turned on, and one or more working modes. The fragrance is identical to or different from that produced by other aromatherapy device of the one or more aromatherapy devices.

18 Claims, 10 Drawing Sheets

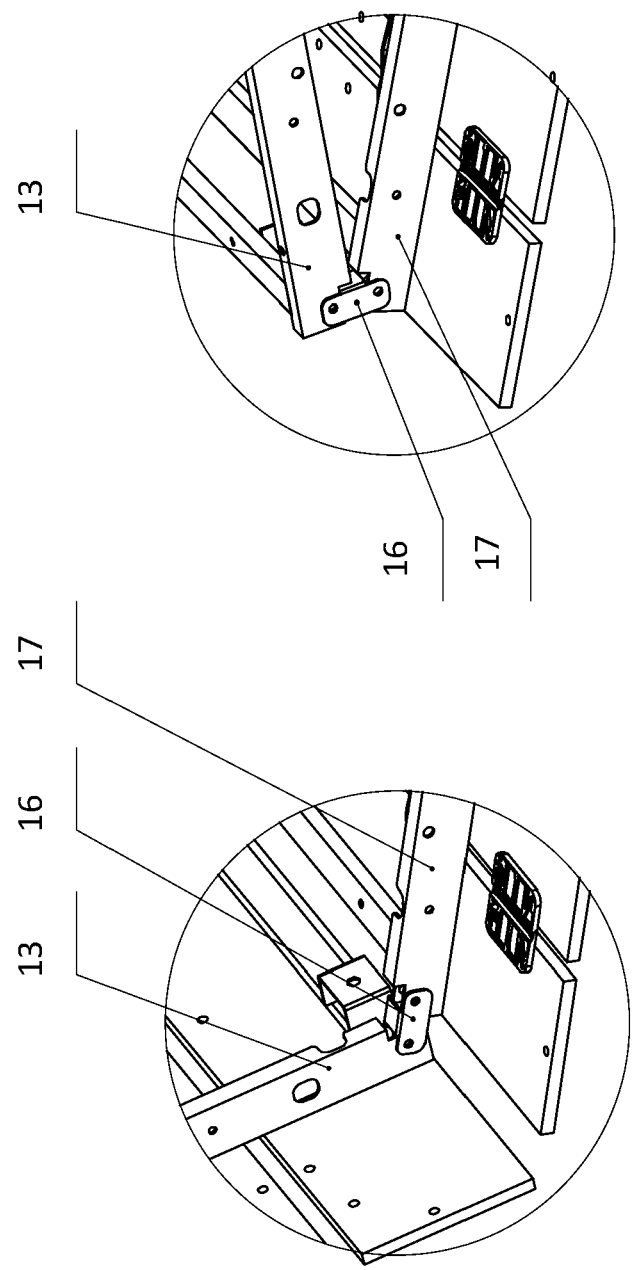

ADJUSTABLE BED WITH AROMATHERAPY SYSTEM

CROSS-REFERENCE TO RELATED PATENT APPLICATIONS

This application claims priority to and the benefit of U.S. Provisional Patent Application Ser. No. 62/889,145, filed Aug. 20, 2019, which is incorporated herein in its entirety by reference.

FIELD OF THE INVENTION

The invention generally relates to a bed, and more particular to an adjustable bed with an aromatherapy system.

BACKGROUND OF THE INVENTION

Sleep is critical for people in every aspect of their lives. Beds are necessary furniture for people to sleep on. Thus, it is beneficial and desirable for people to have a bed system that is capable of adjusting body positions based on user's sleep preference so that the user achieves maximum comfort during sleep. In addition, it is also beneficial and desirable that the bed system has therapeutic functions to promote health and well-being of a user.

SUMMARY OF THE INVENTION

The invention, in one aspect, relates to an adjustable bed comprising a frame structure; a plurality of platforms disposed on the frame structure; and an adjustable assembly coupled with the frame structure and the plurality of platforms for operably adjusting one or more of the plurality of platforms in desired positions; and an aromatherapy system attached onto the one or more platforms for producing desired fragrance in a surrounding space of the adjustable bed so as to promote health and well-being of a user.

In one embodiment, the aromatherapy system is an electric aromatherapy system comprising one or more aromatherapy devices.

In one embodiment, each aromatherapy device is configured to produce a fragrance when said aromatherapy device is turned on. The fragrance is identical to or different from that produced by other aromatherapy device of the one or more aromatherapy devices.

In one embodiment, each aromatherapy device has one or more working modes. The one or more working modes comprises a first working mode in which said aromatherapy device is turned on or turned off based on the user's instruction; a second working mode in which said aromatherapy device is turned on for a first period of time, and then turned off; and a third working mode in which said aromatherapy device is turned on for a second period of time regularly in a third period of time.

In one embodiment, each aromatherapy device comprises a container for containing an aromatic substance; a diffuser coupled to the container for operably heating the aromatic substance therein so as to produce the fragrance; and one or more indicators, each indicator for indicating one of the one or more working modes of said aromatherapy device.

In one embodiment, each aromatherapy device is controllable to operate in one of the one or more working modes by a remote control or an APP.

In one embodiment, the adjustable assembly comprises a back lifting assembly and a leg lifting assembly. The back lifting assembly comprises a back lifting bracket pivotally connected to the frame structure, and a back lifting actuator pivotally connected between the back lifting bracket and the frame structure for operably driving the back lifting bracket to pivotally move in an upward rotating direction or a downward rotating direction relative to the frame structure. The leg lifting assembly comprises a leg lifting bracket pivotally connected to the frame structure, and a leg lifting actuator pivotally connected between the leg lifting bracket and the frame structure for operably driving the leg lifting bracket to pivotally move in an upward rotating direction or a downward rotating direction relative to the frame structure.

In one embodiment, the back lifting bracket comprises a middle bar and a pair of swing arms, wherein the pair of swing arms is transversely spaced and longitudinally extended, and rigidly connected to ends of the transversely extending middle bar, and each of the pair of swing arms has a first end portion and an opposite, second end portion, wherein the first end portion of each swing arm is pivotally mounted to the frame structure. The back lifting actuator comprises a motor member, an outer tube extending from the motor member, an activation rod received in the outer tube, engaged with the motor member and configured to be telescopically movable relative to said outer tube according to a direction of motor rotation, wherein the motor member is pivotally connected to the frame structure, and the activation rod has a distal end portion pivotally connected to the middle bar of the back lifting bracket, or wherein the motor member is pivotally connected to the middle bar of the back lifting bracket, and the activation rod has a distal end portion pivotally connected to the frame structure.

In one embodiment, the swing arms are in an arc-shaped design.

In one embodiment, the second end portion of at least one of the swing arms is equipped with a first lifting wheel and a second lifting wheel.

In one embodiment, the leg lifting bracket comprises a middle bar and a pair of swing arms, wherein the pair of swing arms is transversely spaced and longitudinally extended, and rigidly connected to ends of the transversely extending middle bar, and each of the pair of swing arms has a first end portion and an opposite, second end portion, wherein the first end portion of each swing arm is pivotally mounted to the frame structure. The leg lifting actuator comprises a motor member, an outer tube extending from the motor member, an activation rod received in the outer tube, engaged with the motor member and configured to be telescopically movable relative to said outer tube according to a direction of motor rotation, wherein the motor member is pivotally connected to the frame structure, and the activation rod has a distal end portion pivotally connected to the middle bar of the leg lifting bracket, or wherein the motor member is pivotally connected to the middle bar of the leg lifting bracket, and the activation rod has a distal end portion pivotally connected to the frame structure.

In one embodiment, the second end portion of at least one of the swing arms is equipped with a leg lifting wheel.

In one embodiment, the frame structure comprises an upper rail, a lower rail, and a pair of side rails; wherein the upper rail and the lower rail are longitudinally spaced and transversely extended, and the pair of side rails is transversely spaced and longitudinally extended, and rigidly connected to the upper rail and the lower rail, such that the upper rail and the lower rail and the pair of side rails are co-planar in a rectangle form. The back lifting bracket of the back lifting assembly is pivotally connected to the pair of side rails of the frame structure, and the back lifting actuator of the back lifting assembly is pivotally connected between the back lifting bracket and the upper rail of the frame structure. The leg lifting bracket of the leg lifting assembly is pivotally connected to the pair of side rails of the frame structure, and the leg lifting actuator of the leg lifting assembly is pivotally connected between the leg lifting bracket and the lower rail of the frame structure.

In one embodiment, the frame structure comprises a back frame, and a leg frame. Each of the back frame and the leg frame comprises an upper rail, a lower rail, and a pair of side rails; wherein the upper rail and the lower rail are longitudinally spaced and transversely extended, and the pair of side rails is transversely spaced and longitudinally extended, and rigidly connected to the upper rail and the lower rail, such that the upper rail and the lower rail and the pair of side rails are co-planar in a rectangle form. The back lifting bracket of the back lifting assembly is pivotally connected to the pair of side rails of the back frame, and the back lifting actuator of the back lifting assembly is pivotally connected between the back lifting bracket and the upper rail of the back frame. The leg lifting bracket of the leg lifting assembly is pivotally connected to the pair of side rails of the leg frame, and the leg lifting actuator of the leg lifting assembly is pivotally connected between the leg lifting bracket and the lower rail of the leg frame.

In one embodiment, the frame structure further comprises a folding mechanism connecting the back frame and the leg frame such that the back frame and the leg frame are pivotably foldable to one another at the folding mechanism.

In one embodiment, the plurality of platforms comprises a back platform movably disposed on the back lifting bracket; an upper seat platform mounted on the frame structure and hinged with the back platform; a lower seat platform mounted on the frame structure and being adjacent to the upper seat platform; a thigh platform disposed on the leg lifting bracket and hinged with the lower seat platform; and a leg platform hinged with the thigh platform.

In one embodiment, the leg lifting assembly further comprises a leg support member having a first end pivotally connected to the frame structure, and an opposite, second end pivotally connected to the leg platform.

In one embodiment, the adjustable bed further comprises at least one massage assembly attached to at least one of the plurality of platforms for providing massage effects to the user.

In one embodiment, at least one massage assembly comprises a massage motor, an elastic belt, a massage motor cover, a velcro loop surface, a foam house, a velcro hook surface, and a plywood decking. The velcro loop surface and the massage motor cover are connected, a side of the massage motor passes through an opening of the massage motor cover, the elastic belt passes through the side of the massage motor, the velcro hook surface is fixed onto the plywood decking, the foam house is placed inside a hole of the plywood decking, the massage motor is placed inside a hole of the foam house so that the velcro loop surface and the velcro hook surface are fit together, and the massage motor is fastened onto the plywood decking.

In one embodiment, the adjustable bed also comprises controller configured to control operations of the back lifting actuator, the leg lifting actuator, the aromatherapy system, and at least one massage assembly, respectively, so as to lift individually or cooperatively the head lifting platform, the thigh platform, and the leg platform in desired positions, to produce the fragrance in the surrounding space of the adjustable bed, and to provide the massage effects to the user.

These and other aspects of the invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIGS. 10-11 shows schematically and partially two folding states of the frame structure shown in FIG. 8 in a folding state.

DETAILED DESCRIPTION OF THE INVENTION

Figure 1:
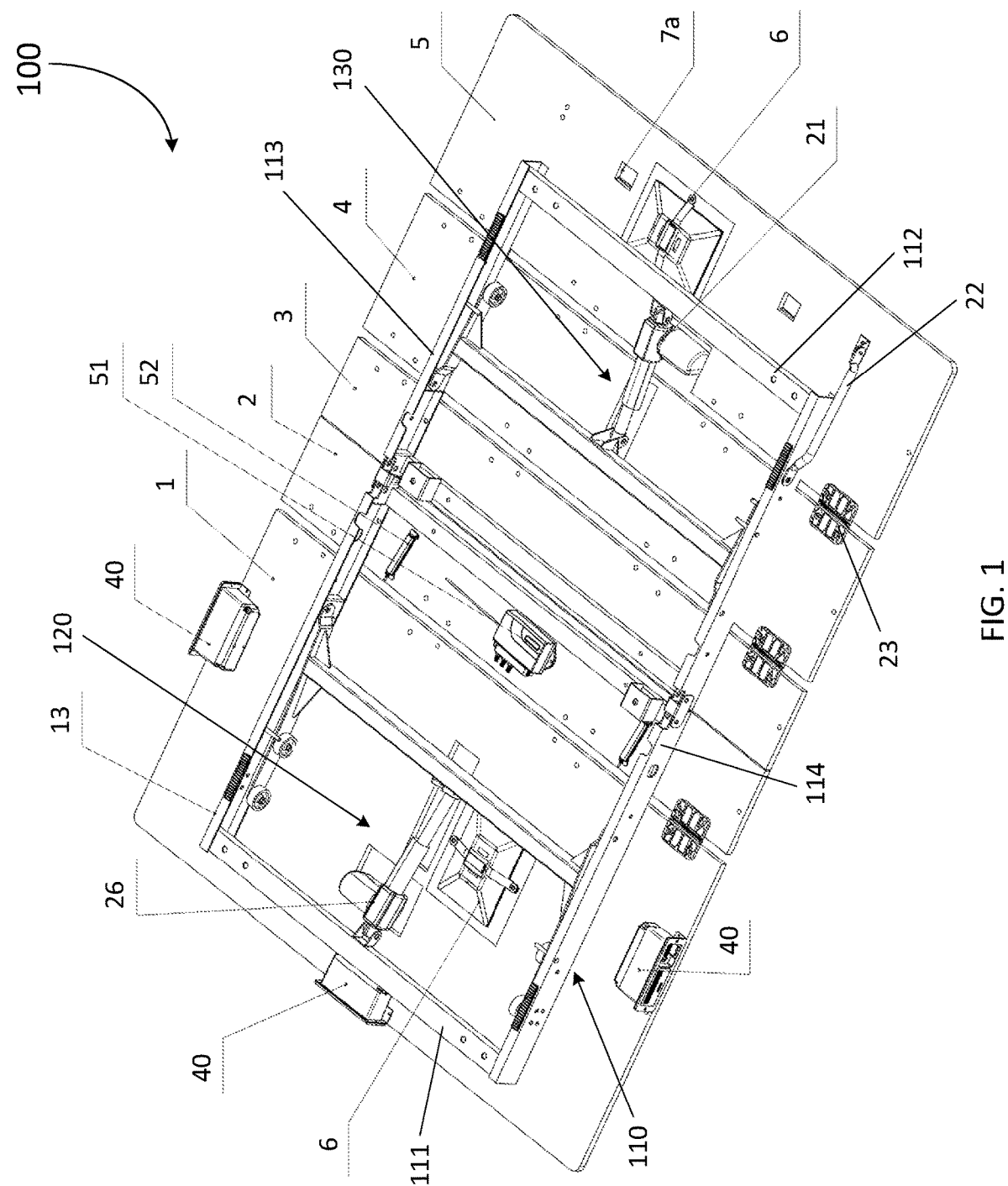
FIG. 1 shows schematically a rear perspective view of an adjustable bed according to one embodiment of the invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about" "substantially" or "approximately" can be inferred if not expressly stated.

The description will be made as to the embodiments of the invention in conjunction with the accompanying drawings in FIGS. 1-13. In accordance with the purposes of this invention, as embodied and broadly described herein, this invention, in one aspect, relates to an adjustable bed with an aromatherapy system.

Referring to FIG. 1, the adjustable bed 100 includes a frame structure 110, a plurality of platforms 1-5 disposed on the frame structure 110 and an adjustable assembly 120 and 130 coupled with the frame structure 110 and the plurality of platforms 1-5 for operably adjusting one or more of the plurality of platforms 1-5 in desired positions; and an aromatherapy system 40 attached onto the one or more platforms 1-5 for producing desired fragrance in a surrounding space of the adjustable bed 100 so as to promote health and well-being of a user. The term "platform" used herein refers to a bed board or board.

Figure 3:
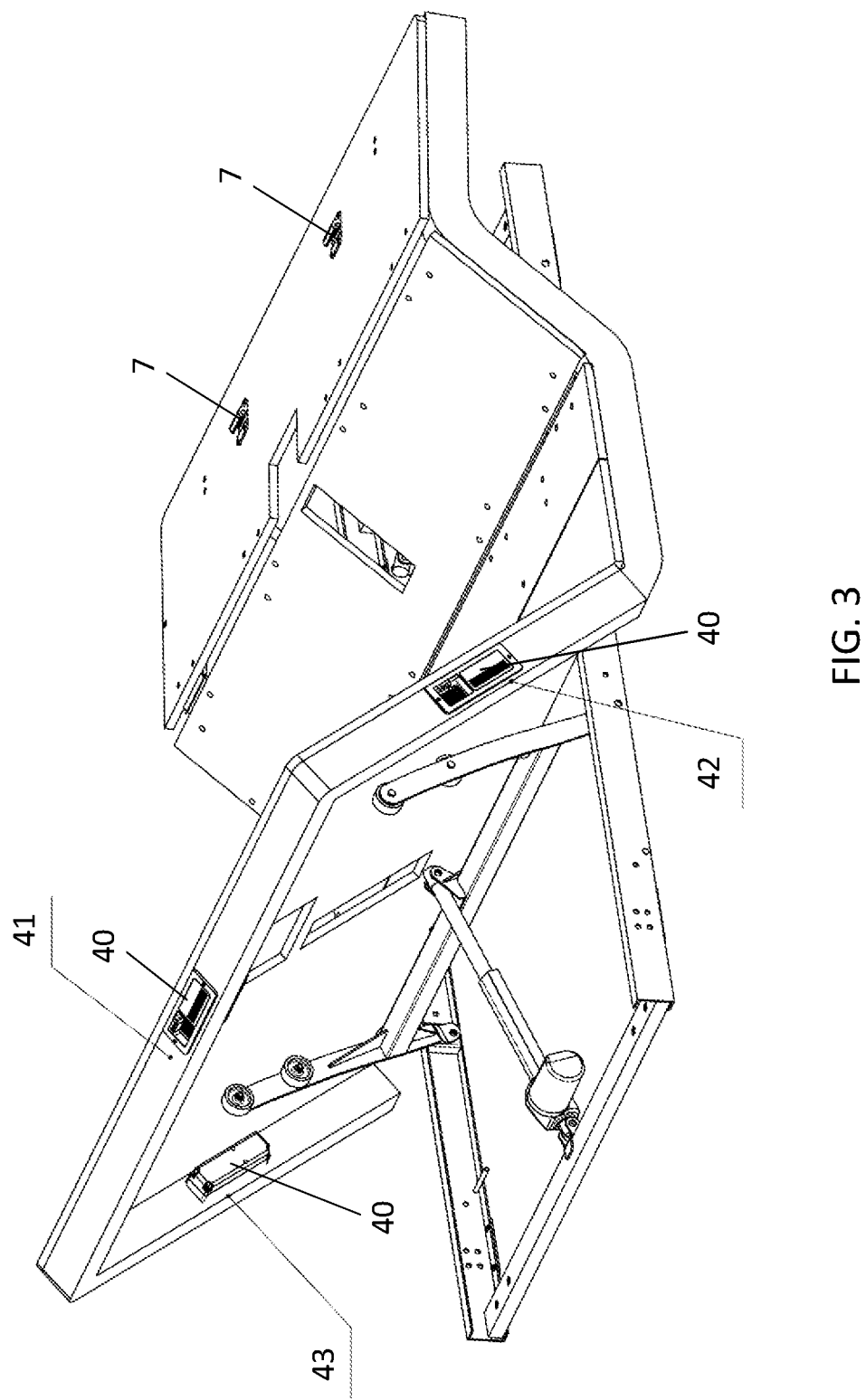
FIG. 3 shows schematically a front perspective view of an adjustable bed according to one embodiment of the invention.
Figure 4:
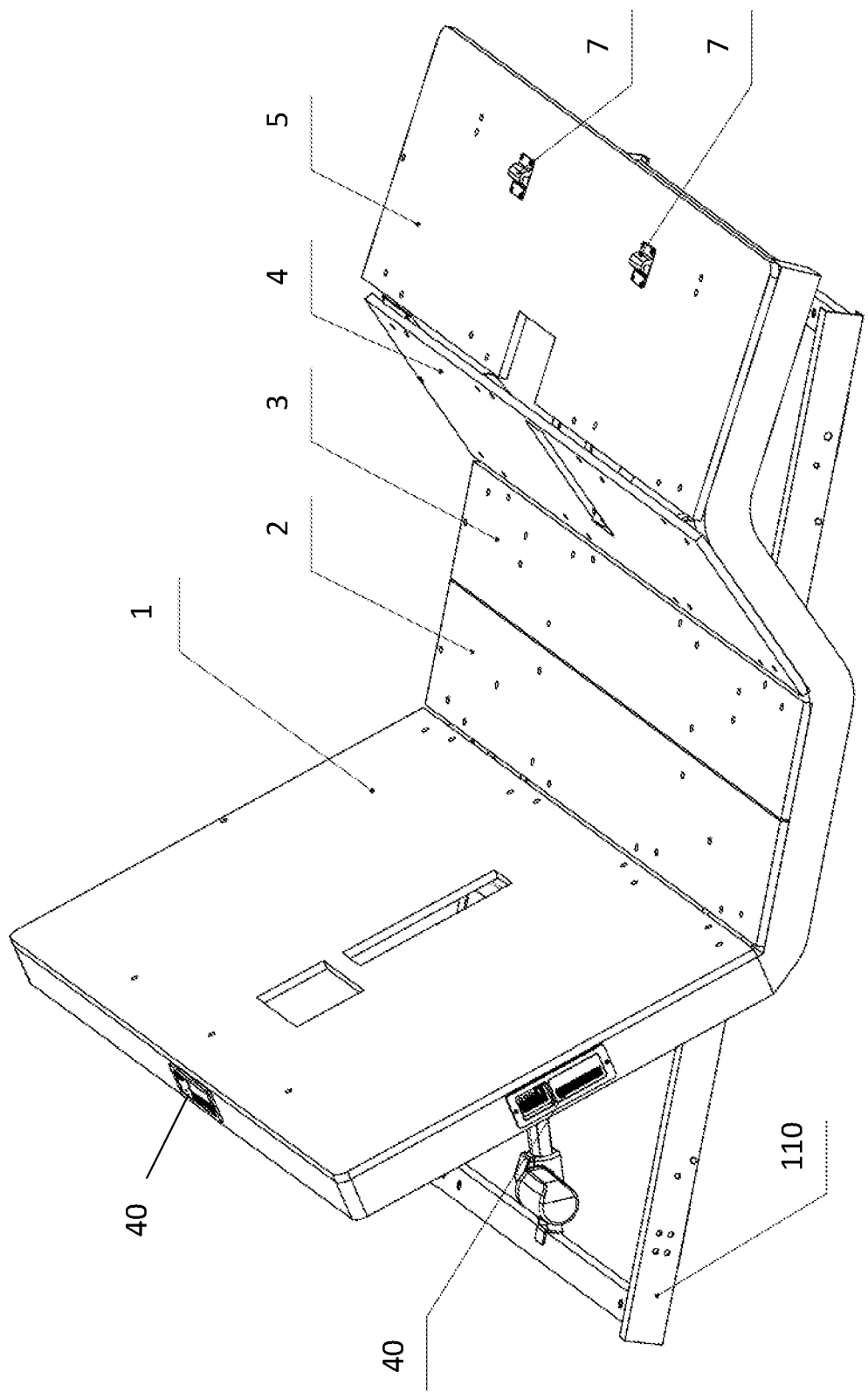
FIG. 4 shows schematically another front perspective view of the adjustable bed shown in FIG. 3.

In some embodiments, the aromatherapy system is an electric aromatherapy system comprising one or more aromatherapy devices 40. For example, as shown in FIG. 1, three aromatherapy devices 40 are employed and attached onto the back platform 1. It should be noted that other number of the aromatherapy devices 40 can also be utilized to practice the invention. In addition, the aromatherapy devices 40 can also be attached onto other platforms, or the frame structure 110. In addition, as shown in FIGS. 3-4, the edges of the plurality of platforms 1-5 are provided with side boards 41-42 for better appearance.

In some embodiments, each aromatherapy device is configured to produce a fragrance when said aromatherapy device is turned on. The fragrance is identical to or different from that produced by other aromatherapy device of the one or more aromatherapy devices.

In some embodiments, each aromatherapy device has one or more working modes. The one or more working modes comprises a first working mode in which said aromatherapy device is turned on or turned off based on the user's instruction; a second working mode in which said aromatherapy device is turned on for a first period of time (e.g., 1 minute), and then turned off; and a third working mode in which said aromatherapy device is turned on for a second period of time (e.g., 1 minute) regularly in each and every third period of time (e.g., each and every 2 hours).

In some embodiments, each aromatherapy device 40 can be individually or cooperatively controlled to operate in one of the one or more working modes by a remote control or an APP.

Figure 5:
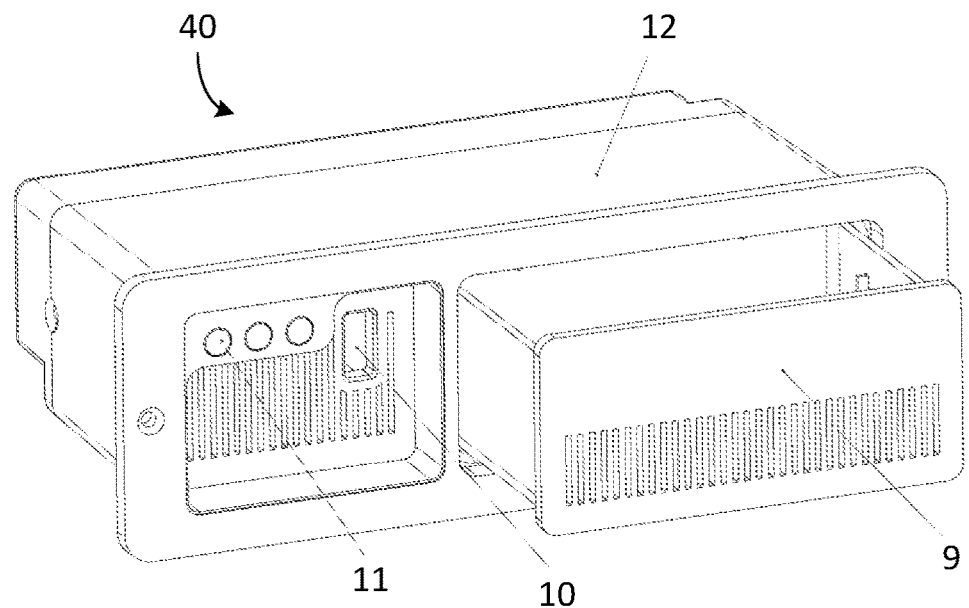
FIG. 5 shows schematically a front perspective view of an aromatherapy device according to one embodiment of the invention.

In one embodiment shown in FIG. 5, each aromatherapy device 40 comprises a container 9 for containing an aromatic substance; a diffuser coupled to the container 9 for operably heating the aromatic substance therein so as to produce the fragrance; and one or more indicators 11 with each indicator for indicating one of the one or more working modes of said aromatherapy device 40. Each aromatherapy device 40 also comprises a housing 12 for accommodating the container 9 and the indicators 11. The container 9 is detachable from the housing 12. In addition, each aromatherapy device 40 includes one or more USB port 10. According to the invention, each aromatherapy device 40 can contain an aromatic substance that is identical to or different from that of the aromatherapy devices 40.

The aromatic substance can be a substance extracted natural plants such as aromatic essential oils, or a chemically synthesized material. It is proven that aromatherapy using aromatic essential oils medicinally improves the health of the body, mind, and spirit, and has benefits including, but is not limited to, managing pain, improving sleep quality, reducing stress, agitation, and anxiety, soothing sore joints, treating headaches and migraines, and boosting immunity.

The capability of producing different fragrances from the one or more aromatherapy devices 40 and the controllability of the one or more aromatherapy devices 40 have particular therapeutic benefits for the user. For example, during wake up time, one aromatherapy devices 40 can be configured to produce a fresh air fragrance, while during a sleep time, the other aromatherapy devices 40 can be configured to produce a fragrance improving sleep quality of the user.

Figure 8:
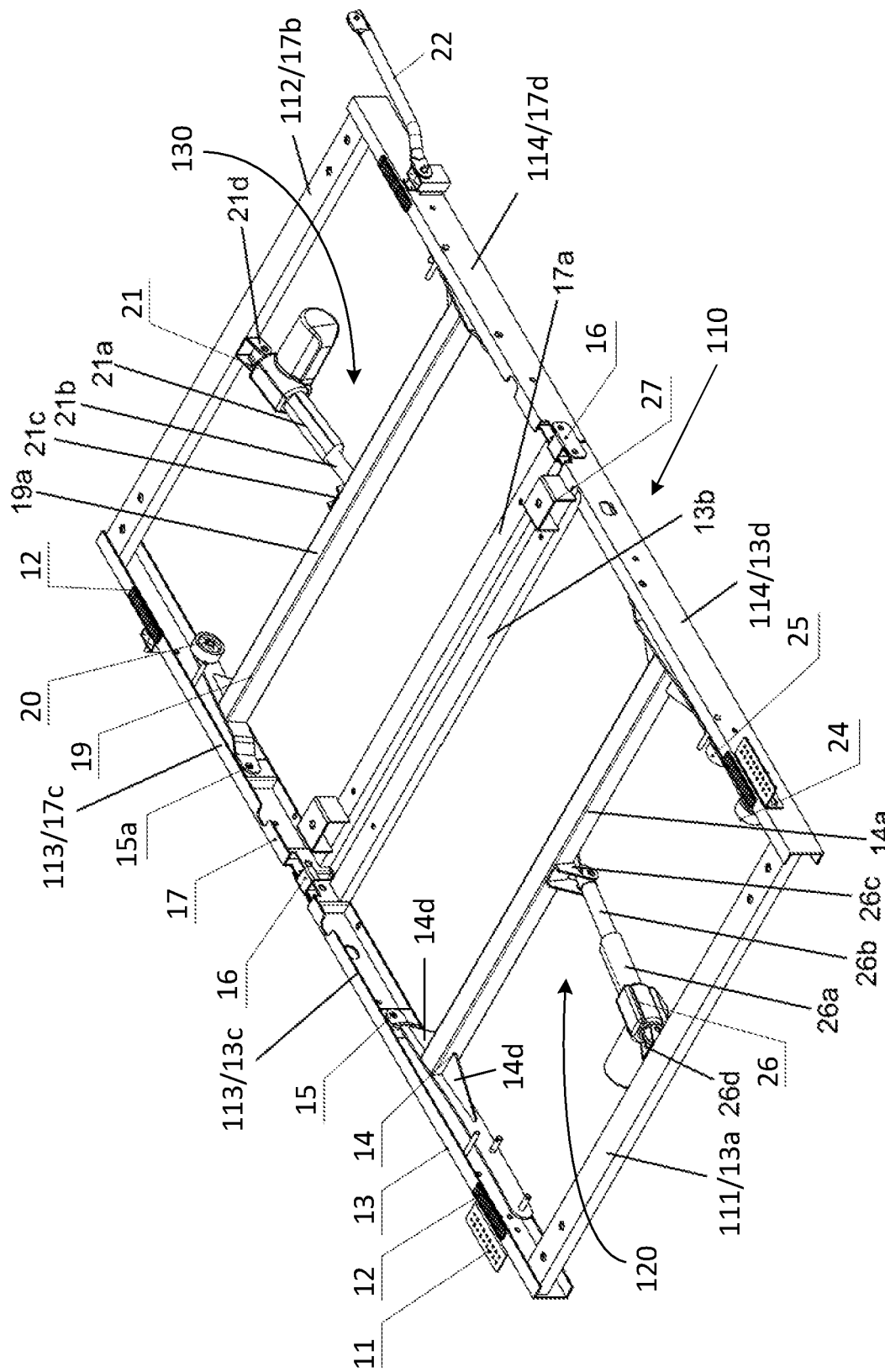
FIG. 8 shows schematically a front perspective view of a frame structure of the adjustable bed shown in FIG. 1 in a flat state.
Figure 9:
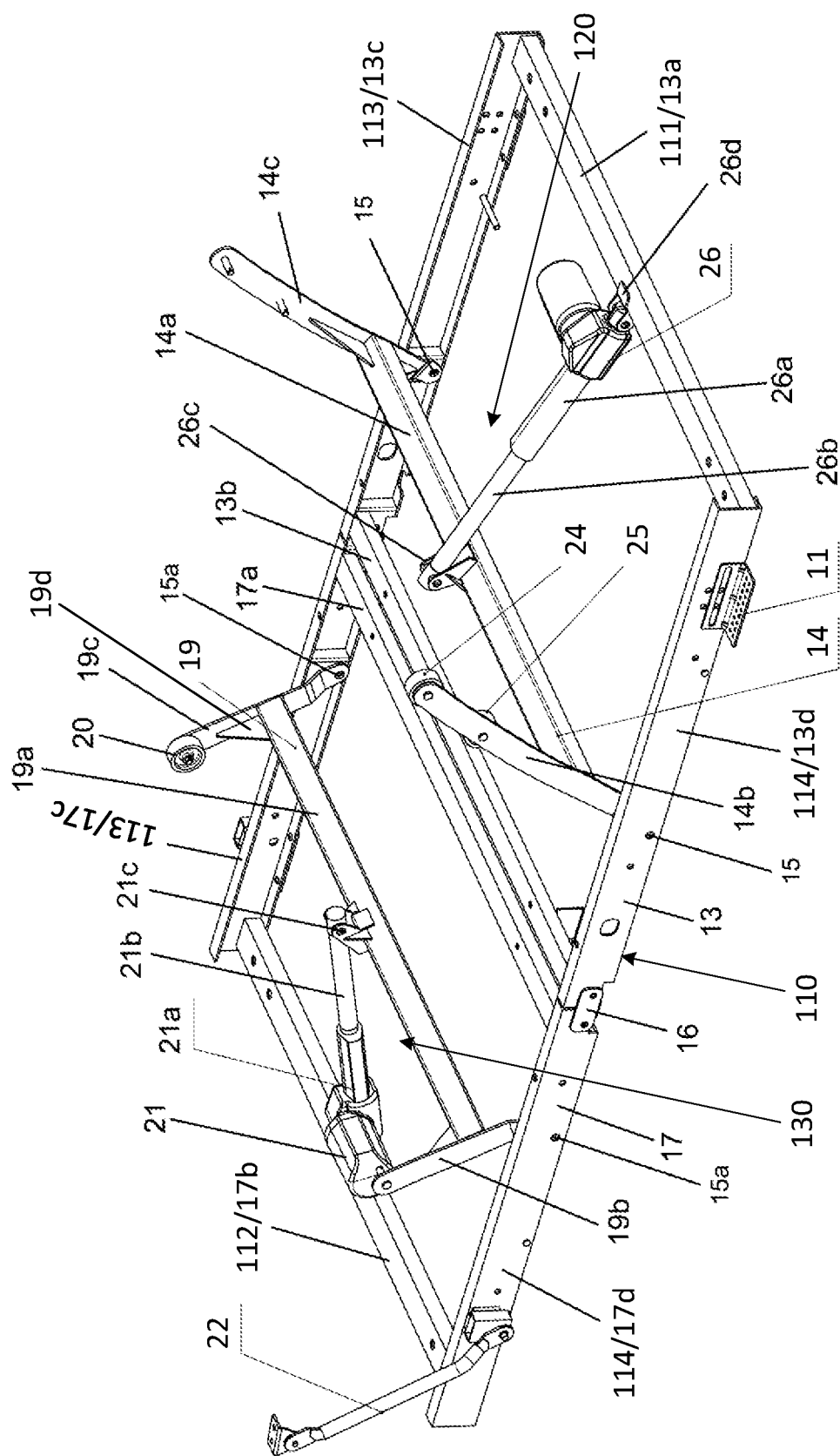
FIG. 9 shows schematically a front perspective view of the frame structure shown in FIG. 8 in an adjusting state.
Figure 12:
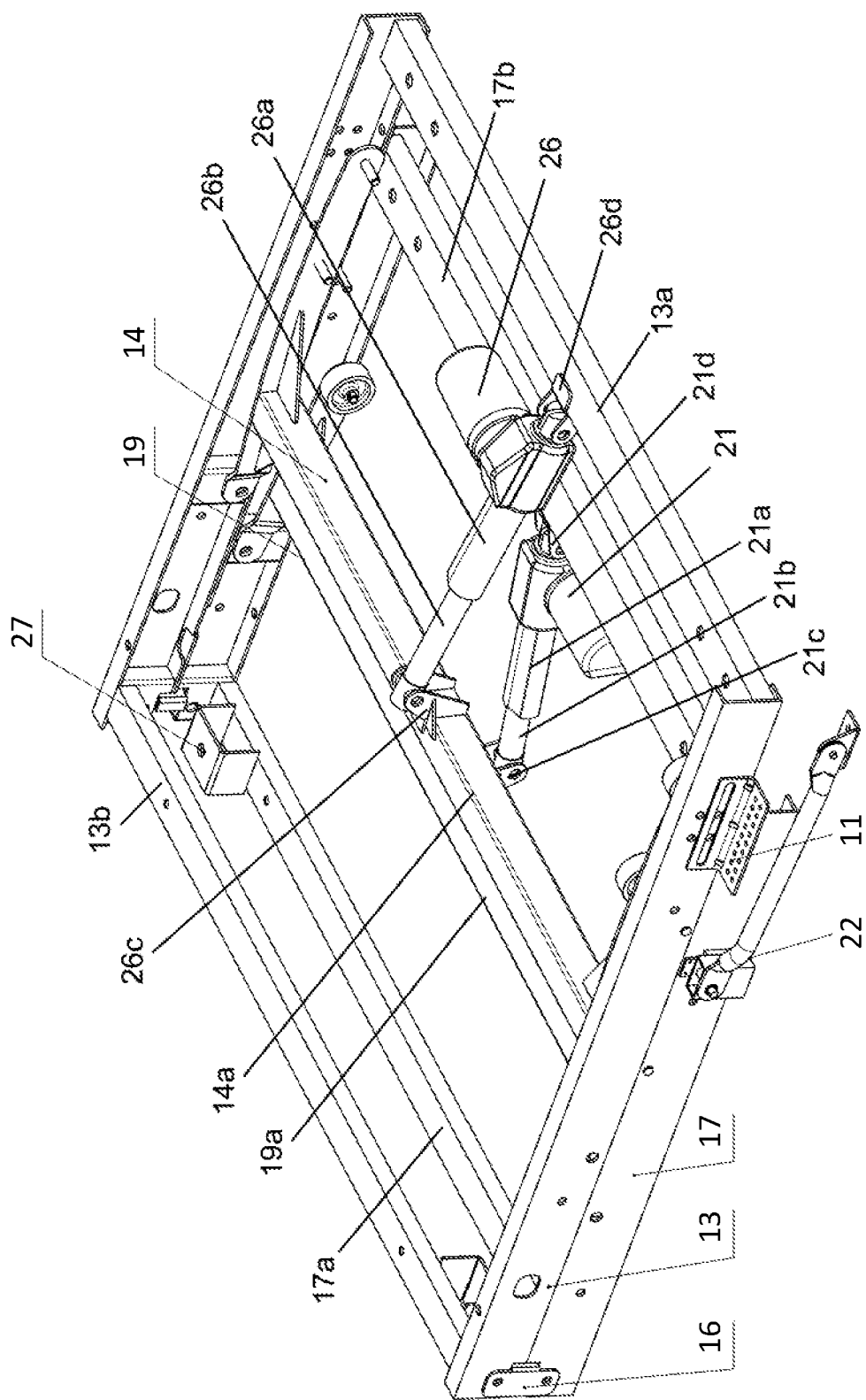
FIG. 12 shows schematically a front perspective view of the frame structure shown in FIG. 8 in a folding state.

In one embodiment, as shown FIGS. 1 and 8-9, the frame structure 110 includes an upper rail 111, a lower rail 112, and a pair of side rails 113 and 114. The upper rail 111 and the lower rail 112 are longitudinally spaced and transversely extended, and the pair of side rails 113 and 114 is transversely spaced and longitudinally extended, and rigidly connected to the upper rail 111 and the lower rail 112, such that the upper rail 111 and the lower rail 112 and the pair of side rails 113 and 114 are co-planar in a rectangle form. Preferably, the connection of the pair of side rails 113 and 114 to the upper and lower rails 111 and 112 is by welding ends of the upper rail 111 onto end portions of the pair of side rails 113 and 114, and welding ends of the lower rail 112 onto opposite end portions of the pair of side rails 113 and 114. Other connecting means can also be utilized to practice the invention.

The adjustable assembly includes a back lifting assembly 120 and a leg lifting assembly 130.

The back lifting assembly 120 has a back lifting bracket 14 pivotally connected to the side rails 113 and 114 of the frame structure 110, and a back lifting actuator 26 pivotally connected between the back lifting bracket 14 and the upper rail 111 of the frame structure 110 for operably driving the back lifting bracket 14 to pivotally move in an upward rotating direction or a downward rotating direction relative to the frame structure 110.

The back lifting bracket 14 includes a middle bar 14a and a pair of swing arms 14b and 14c. Each of the pair of swing arms 14b and 14c is in an arc-shaped design. The pair of swing arms 14b and 14c is transversely spaced and longitudinally extended, and rigidly connected to ends of the transversely extending middle bar 14a in an H-shaped form. Each of the pair of swing arms 14b and 14c has a first end portion and an opposite, second end portion. The first end portion of each swing arm 14b or 14c is pivotally mounted to a respective one of the side rails 113 and 114 of the frame structure 110 through a pivot 15. The second end portion of at least one of the swing arms 14b and 14c is equipped with a first lifting wheel 25 and a second lifting wheel 24. The drawings of FIGS. 1 and 8-9 show only the second end portion of the swing arms 14b is equipped with a first lifting wheel 25 and a second lifting wheel 24. Practically, the second end portion of the swing arms 14c may also be equipped with the first lifting wheel 25 and the second lifting wheel 24. In addition, each of the pair of swing arms 14b and 14c may be reinforced by a pair of reinforcing pieces 14d rigidly connected to an end portion of the middle bar 14a on either side.

The back lifting actuator includes a motor member 26, an outer tube 26a extending from the motor member 26, and an activation rod 26b received in the outer tube 26a, engaged with the motor member 26 and configured to be telescopically movable relative to said outer tube 26a according to a direction of motor rotation. The motor member 26 is pivotally connected to the upper rail 111 of the frame structure 110 through a first bracket 26d. The activation rod 26b has a distal end portion pivotally connected to the middle bar 14a of the back lifting bracket 14 through a second bracket 26c.

The leg lifting assembly 130 has a leg lifting bracket 19 pivotally connected to the side rails 113 and 114 of the frame structure 110, and a leg lifting actuator 21 pivotally connected between the leg lifting bracket 19 and the lower rail 112 of the frame structure 110 for operably driving the leg lifting bracket 19 to pivotally move in an upward rotating direction or a downward rotating direction relative to the frame structure 110.

The leg lifting bracket 19 includes a middle bar 19a and a pair of swing arms 19b and 19c. The pair of swing arms 19b and 19c is transversely spaced and longitudinally extended, and rigidly connected to ends of the transversely extending middle bar 19a in an H-shaped form. Each of the pair of swing arms 19b and 19c has a first end portion and an opposite, second end portion. The first end portion of each swing arm 19b or 19c is pivotally mounted to a respective one of the side rails 113 and 114 of the frame structure 110 through a pivot 15a. The second end portion of at least one of the swing arms 19b and 19c is equipped with a leg lifting wheel 20. The drawings of FIGS. 1 and 8-9 show only the second end portion of the swing arms 19c is equipped with the leg lifting wheel 20. Practically, the second end portion of the swing arms 19b may also be equipped with the leg lifting wheel 20. In addition, each of the pair of swing arms 19b and 19c may be reinforced by a reinforcing piece rigidly connected to an end portion of the middle bar 19a on the side not pivotally mounted through a pivot 15a.

The leg lifting actuator includes a motor member 21, an outer tube 21a extending from the motor member 21, and an activation rod 21b received in the outer tube 21a, engaged with the motor member 21 and configured to be telescopically movable relative to said outer tube 21a according to a direction of motor rotation. The motor member 21 is pivotally connected to the lower rail 112 of the frame structure 110 through a first bracket 21d. The activation rod 21b has a distal end portion pivotally connected to the middle bar 19a of the leg lifting bracket 19 through a second bracket 21c.

In another embodiment, as shown in FIGS. 8-12, the frame structure 110 includes a back frame 13 and a leg frame 17 and a folding mechanism 16 connecting the back frame 13 and the leg frame 17 such that the back frame 13 and the leg frame 17 are pivotably foldable to one another at the folding mechanism 16. Preferably, the folding mechanism 16 is a hinge bracket. When folding the adjustable bed, the back frame 13 rotates around the rotation center of the folding mechanism 16 (FIG. 10). When the side of the back frame 13 touches the upper folding edge of the folding mechanism 16 (i.e., at a 90° position), the back frame 13 and the folding mechanism 16 continue to rotate around another rotation center (FIG. 11) until they overlap the leg frame 17. The upper folding edge of the folding mechanism 16 limits the position during the folding process. When the adjustable bed is completely folded, there is no gap between the back frame 13 and the leg frame 17, which minimizes the folded thickness. Other connecting means and other types of folding mechanism can also be utilized to practice the invention.

The back frame 13 includes an upper rail 13a, a lower rail 13b, and a pair of side rails 13c and 13d. The upper rail 13a and the lower rail 13b are longitudinally spaced and transversely extended, and the pair of side rails 13c and 13d is transversely spaced and longitudinally extended, and rigidly connected to the upper rail 13a and the lower rail 13b, such that the upper rail 13a and the lower rail 13b and the pair of side rails 13c and 13d are co-planar in a rectangle form. Preferably, the connection of the pair of side rails 13c and 13d to the upper and lower rails 13a and 13b is by welding ends of the upper rail 13a onto end portions of the pair of side rails 13c and 13d, and welding ends of the lower rail 13b onto opposite end portions of the pair of side rails 13c and 13d. Other connecting means can also be utilized to practice the invention.

The back lifting assembly 120 has a back lifting bracket 14 pivotally connected to the back frame 13, and a back lifting actuator pivotally connected between the back lifting bracket 14 and the back frame 13 for operably driving the back lifting bracket 14 to pivotally move in an upward rotating direction or a downward rotating direction relative to the back frame 13.

The back lifting bracket 14 includes a middle bar 14a and a pair of swing arms 14b and 14c. Each of the pair of swing arms 14b and 14c is in an arc-shaped design. The pair of swing arms 14b and 14c is transversely spaced and longitudinally extended, and rigidly connected to ends of the transversely extending middle bar 14a in an H-shaped form. Each of the pair of swing arms 14b and 14c has a first end portion and an opposite, second end portion. The first end portion of each swing arm 14b or 14c is pivotally mounted to a respective one of the side rails 13c and 13d of the back frame 13 through a pivot 15. The second end portion of at least one of the swing arms 14b and 14c is equipped with a first lifting wheel 25 and a second lifting wheel 24. The drawings of FIGS. 8-9 show only the second end portion of the swing arms 14b is equipped with a first lifting wheel 25 and a second lifting wheel 24. Practically, the second end portion of the swing arms 14c may also be equipped with the first lifting wheel 25 and the second lifting wheel 24. In addition, each of the pair of swing arms 14b and 14c may be reinforced by a pair of reinforcing pieces 14d (FIG. 8) rigidly connected to an end portion of the middle bar 14a on either side.

The back lifting actuator includes a motor member 26, an outer tube 26a extending from the motor member 26, and an activation rod 26b received in the outer tube 26a, engaged with the motor member 26 and configured to be telescopically movable relative to said outer tube 26a according to a direction of motor rotation. The motor member 26 is pivotally connected to the upper rail 13a of the back frame 13 through a first bracket 26d. The activation rod 26b has a distal end portion pivotally connected to the middle bar 14a of the back lifting bracket 14 through a second bracket 26c.

The leg frame 17 includes an upper rail 17a, a lower rail 17b, and a pair of side rails 17c and 17d. The upper rail 17a and the lower rail 17b are longitudinally spaced and transversely extended, and the pair of side rails 17c and 17d is transversely spaced and longitudinally extended, and rigidly connected to the upper rail 17a and the lower rail 17b, such that the upper rail 17a and the lower rail 17b and the pair of side rails 17c and 17d are co-planar in a rectangle form. Preferably, the connection of the pair of side rails 17c and 17d to the upper and lower rails 17a and 17b is by welding ends of the upper rail 17a onto end portions of the pair of side rails 17c and 17d, and welding ends of the lower rail 17b onto opposite end portions of the pair of side rails 17c and 17d. Other connecting means can also be utilized to practice the invention.

The leg lifting assembly 130 has a leg lifting bracket 19 pivotally connected to the leg frame 17, and a leg lifting actuator pivotally connected between the leg lifting bracket 19 and the leg frame 17 for operably driving the leg lifting bracket 19 to pivotally move in an upward rotating direction or a downward rotating direction relative to the leg frame 17.

The leg lifting bracket 19 includes a middle bar 19a and a pair of swing arms 19b and 19c. The pair of swing arms 19b and 19c is transversely spaced and longitudinally extended, and rigidly connected to ends of the transversely extending middle bar 19a in an H-shaped form. Each of the pair of swing arms 19b and 19c has a first end portion and an opposite, second end portion. The first end portion of each swing arm 19b or 19c is pivotally mounted to a respective one of the side rails 17c and 17d of the leg frame 17 through a pivot 15a. The second end portion of at least one of the swing arms 19b and 19c is equipped with a leg lifting wheel 20. The drawings of FIGS. 8-9 show only the second end portion of the swing arms 19c is equipped with the leg lifting wheel 20. Practically, the second end portion of the swing arms 19b may also be equipped with the leg lifting wheel 20. In addition, each of the pair of swing arms 19b and 19c may be reinforced by a reinforcing piece 19d (FIG. 9) rigidly connected to an end portion of the middle bar 19a on the side not pivotally mounted through a pivot 15a.

The leg lifting actuator includes a motor member 21, an outer tube 21a extending from the motor member 21, and an activation rod 21b received in the outer tube 21a, engaged with the motor member 21 and configured to be telescopically movable relative to said outer tube 21a according to a direction of motor rotation. The motor member 21 is pivotally connected to the lower rail 17b of the leg frame 17 through a first bracket 21d. The activation rod 21b has a distal end portion pivotally connected to the middle bar 19a of the leg lifting bracket 19 through a second bracket 21c.

The adjustable bed also includes middle leg brackets 27. One of the middle leg brackets 27 is connected to an end portion of the lower rail 13b closer to the side rail 13d.

Another of the middle leg brackets 27 is connected to an end portion of the upper rail 17a closer to the side rail 17c.

As shown in FIG. 1, the plurality of platforms includes a back platform 1 movably disposed on the back lifting bracket 14; an upper seat platform 2 mounted on the back frame 13 and hinged with the back platform 1 through hinges 23; a lower seat platform 3 mounted on the leg frame 17 and being adjacent to the upper seat platform 2; a thigh platform 4 disposed on the leg lifting bracket and hinged with the lower seat platform 2 through hinges 23; and a leg platform 5 hinged with the thigh platform 4 through hinges 23. As such, the back platform 1 is operably rotatable around a lower side of the back platform 1 in a back platform forward direction (i.e., from a laid back or flat state to a lift state) or a back platform backward direction (i.e., from a lift state to a laid back or flat state); the thigh platform 4 is operably rotatable around the lower side of the thigh platform 4 in a thigh platform forward direction (i.e., from a laid back state to a lift state) or a thigh platform backward direction (i.e., from a lift state to a laid back state); and the leg platform 5 is operably rotatable around a rotating axis of the hinge 23.

In addition, a leg support member 22 is provided to support the leg platform 5. Specifically, the leg support member 22 has a first end pivotally connected to the side rails 17c and 17d of the leg frame 17, and an opposite, second end pivotally connected to the leg platform 5.

As shown in FIG. 1, the adjustable bed 100 further includes at least one massage assembly 6 for providing massage effects to a user of the bed. In the exemplary embodiment, two massage assembly 6 are used. Of them, one massage assembly 6 is disposed on the back platform 1 and the other is disposed on the leg platform 5.

Figure 6:
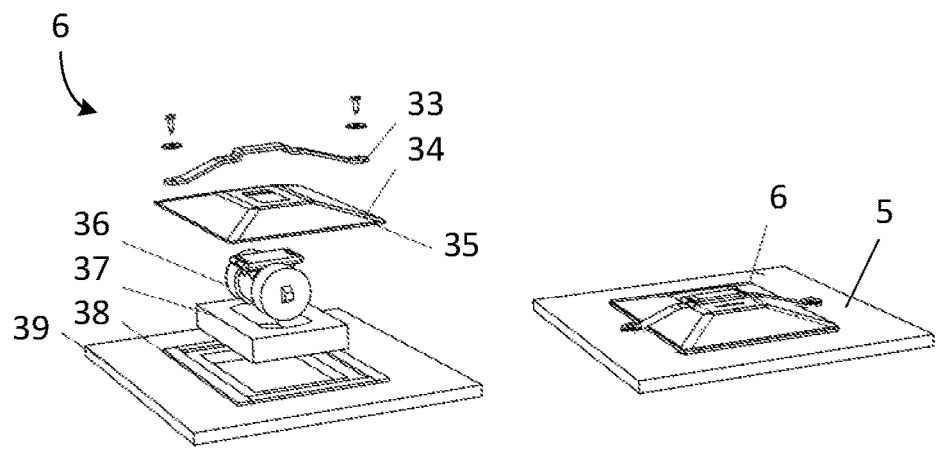
FIG. 6 shows schematically an exploded view and a perspective view of a massage assembly according to one embodiment of the invention.

As shown in FIG. 6, the massage assembly 6 includes a massage motor 36, an elastic belt 33, a massage motor cover 34, a velcro loop surface 35, a foam house 37, a velcro hook surface 38, and a plywood decking 39. The velcro loop surface 35 and the massage motor cover 34 are connected. A side of the massage motor 36 passes through an opening of the massage motor cover 34, and the elastic belt 33 passes through the side of the massage motor 36 (the side of the massage motor 36 has a small opening for the elastic belt to pass through) to connect the components as a whole. Further, the velcro hook surface 38 is fixed onto the plywood decking 39, which may be done by a nail or any other connecting means not limited thereto. The foam house 37 is placed inside a hole of the plywood decking 39, and the massage motor 36 as assembled above is placed inside a hole of the foam house 37 so that the velcro loop surface 35 and the velcro hook surface 38 are fit together. Finally, the massage motor 36 is fastened onto the plywood decking 39, e.g., via a pair of screws and a pair of washers. The massage motor 36 can be easily replaced by simply removing the elastic belt 33 from the side of the massage motor 36 and separating the velcro surfaces.

Figure 2:
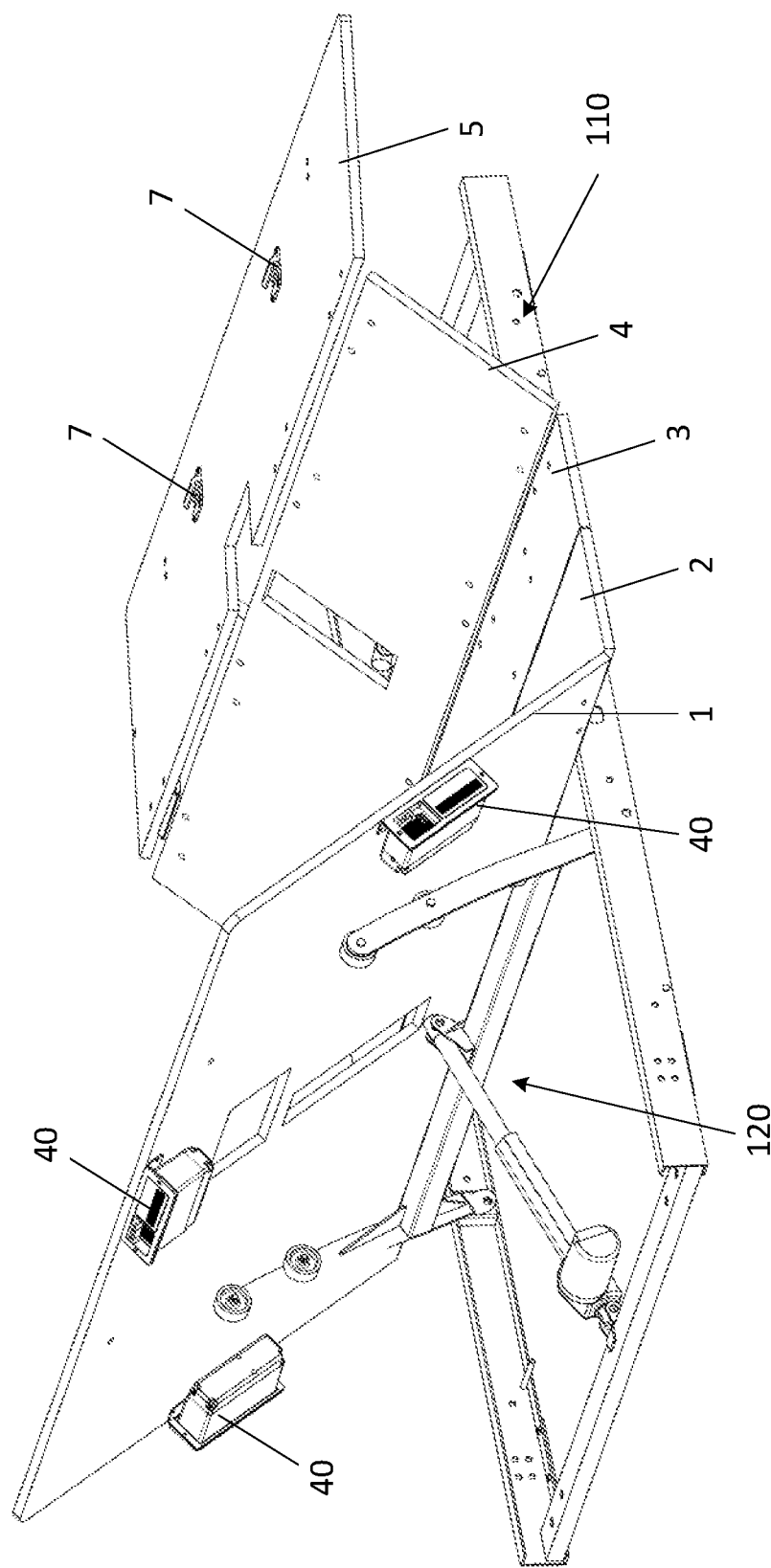
FIG. 2 shows schematically a front perspective view of an adjustable bed according to one embodiment of the invention.
Figure 7:
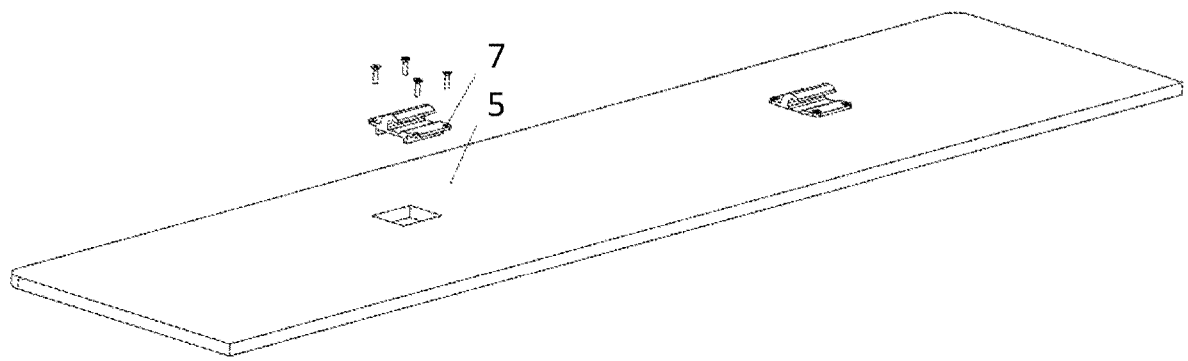
FIG. 7 shows schematically a mattress retainer bar holder attached onto a leg platform according to one embodiment of the invention.

As shown in FIGS. 2-3 and 7, the leg platform 5 is equipped with two mattress retainer bar holder 7 for retaining the mattress on the plurality of platforms 1-5.

The adjustable bed further includes a controller configured to control operations of the back lifting actuator and the leg lifting actuator, respectively, so as to lift individually or cooperatively the head lifting platform 1, the thigh platform 4, and the leg platform 5 in desired positions. A user lying on the adjustable bed can make adjustments as desired.

Figure 13:
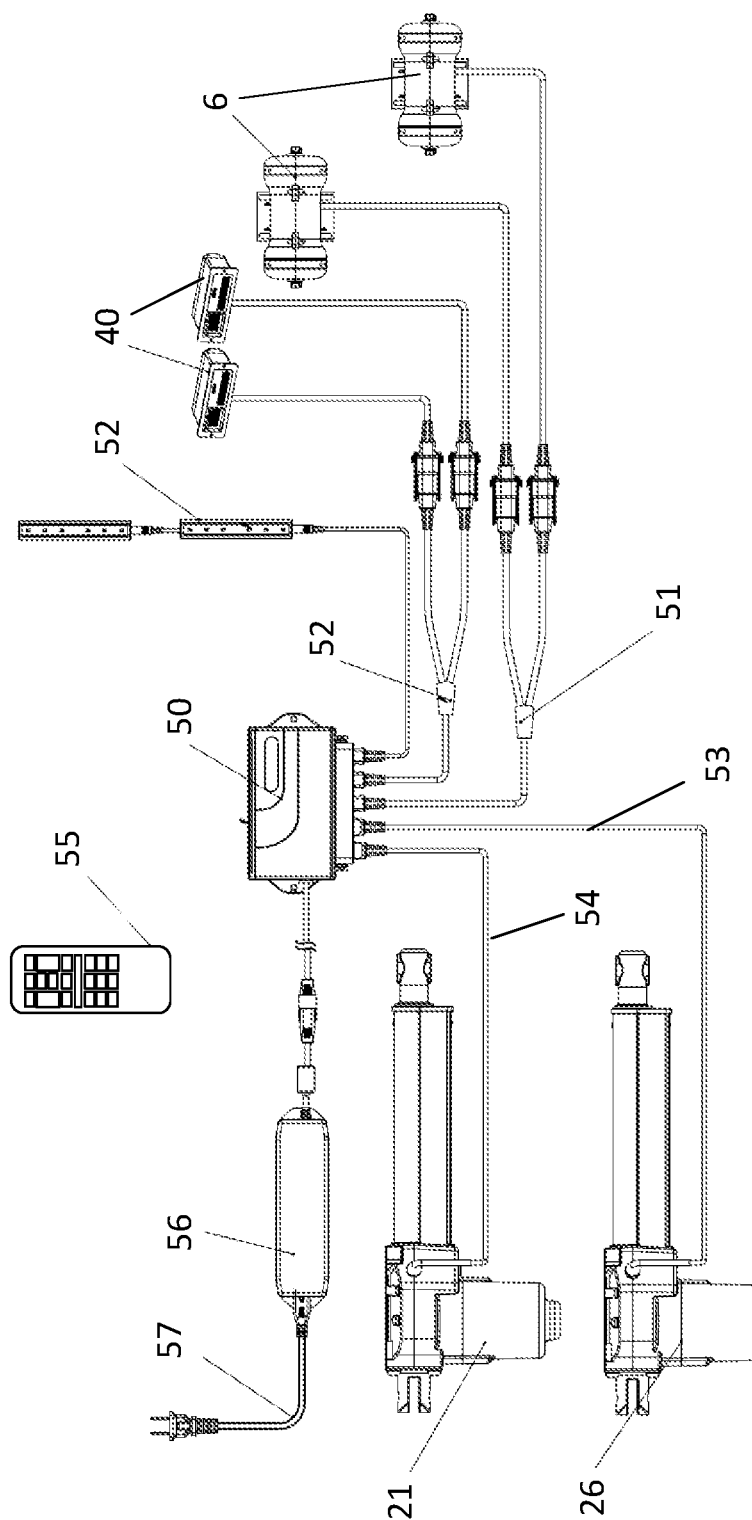
FIG. 13 shows schematically a control system according to one embodiment of the invention.

The adjustable bed system further includes a controlling system, which in one embodiment shown in FIG. 13, includes a controller 183 configured to control operations of the back lifting actuator (motor) 26, the leg lifting actuator (motor) 21, the aromatherapy system 40, and the massage assembly 6, respectively, so as to lift individually or cooperatively the head lifting platform 1, the thigh platform 3, and the leg platform 5 in desired positions, to produce the fragrance in the surrounding space of the adjustable bed, and to provide the massage effects to the user. In one embodiment shown in FIG. 13, the control system includes a power cord 57, a power supply 56, a control box 50, a plurality of connecting cables 51 and 52, and LED lights 50. The control box 50 is powered by the power supply 56 which is in turn connected to any power source via the power cord 57. The back lifting motor 26 and the leg lifting motor 21 are connected to the control box 50 via the plurality of connection cables e.g., the connecting cables 53 and 54. In this way, the user can adjust the bed position via a remote controller 55 or an APP. Alternatively, LED lights 52 can be employed to indicate the working conditions of the back lifting motor 26 and the leg lifting motor 21.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

What is claimed is:

1. An adjustable bed, comprising:
 a frame structure;
 a plurality of platforms disposed on the frame structure; and
 an adjustable assembly coupled with the frame structure and the plurality of platforms for operably adjusting one or more of the plurality of platforms in desired positions; and
 an aromatherapy system attached onto the one or more platforms for producing desired fragrance in a surrounding space of the adjustable bed so as to promote health and well-being of a user,
 wherein the adjustable assembly comprises:
  a back lifting assembly comprising a back lifting bracket pivotally connected to the frame structure, and a back lifting actuator pivotally connected between the back lifting bracket and the frame structure for operably driving the back lifting bracket to pivotally move in an upward rotating direction or a downward rotating direction relative to the frame structure; and
  a leg lifting assembly comprising a leg lifting bracket pivotally connected to the frame structure, and a leg lifting actuator pivotally connected between the leg lifting bracket and the frame structure for operably driving the leg lifting bracket to pivotally move in an upward rotating direction or a downward rotating direction relative to the frame structure;

wherein
the back lifting bracket comprises a middle bar and a pair of swing arms, wherein the pair of swing arms is transversely spaced and longitudinally extended, and rigidly connected to ends of the transversely extending middle bar, and each of the pair of swing arms has a first end portion and an opposite, second end portion, wherein the first end portion of each swing arm is pivotally mounted to the frame structure; and the back lifting actuator comprises a motor member, an outer tube extending from the motor member, an activation rod received in the outer tube, engaged with the motor member and configured to be telescopically movable relative to said outer tube according to a direction of motor rotation, wherein the motor member is pivotally connected to the frame structure, and the activation rod has a distal end portion pivotally connected to the middle bar of the back lifting bracket, or wherein the motor member is pivotally connected to the middle bar of the back lifting bracket, and the activation rod has a distal end portion pivotally connected to the frame structure.

2. The adjustable bed of claim 1, wherein the aromatherapy system is an electric aromatherapy system comprising one or more aromatherapy devices.

3. The adjustable bed of claim 2, wherein each aromatherapy device is configured to produce a fragrance when said aromatherapy device is turned on, wherein the fragrance is identical to or different from that produced by other aromatherapy device of the one or more aromatherapy devices.

4. The adjustable bed of claim 3, wherein each aromatherapy device has one or more working modes, wherein the one or more working modes comprises
a first working mode in which said aromatherapy device is turned on or turned off based on the user's instruction;
a second working mode in which said aromatherapy device is turned on for a first period of time, and then turned off; and
a third working mode in which said aromatherapy device is turned on for a second period of time regularly in a third period of time.

5. The adjustable bed of claim 4, wherein each aromatherapy device comprises
a container for containing an aromatic substance;
a diffuser coupled to the container for operably heating the aromatic substance therein so as to produce the fragrance; and
one or more indicators, each indicator for indicating one of the one or more working modes of said aromatherapy device.

6. The adjustable bed of claim 4, wherein each aromatherapy device is controllable to operate in one of the one or more working modes by a remote control or an APP.

7. The adjustable bed of claim 1, further comprising at least one massage assembly for providing massage effects to the user.

8. The adjustable bed of claim 7, further comprising a controller configured to control operations of the back lifting actuator, the leg lifting actuator, the aromatherapy system, and at least one massage assembly, respectively, so as to lift individually or cooperatively the head lifting platform, the thigh platform, and the leg platform in desired positions, to produce the fragrance in the surrounding space of the adjustable bed, and to provide the massage effects to the user.

9. The adjustable bed of claim 1, wherein the swing arms are in an arc-shaped design.

10. The adjustable bed of claim 9, wherein the second end portion of at least one of the swing arms is equipped with a leg lifting wheel.

11. The adjustable bed of claim 1, wherein
the leg lifting bracket comprises a middle bar and a pair of swing arms, wherein the pair of swing arms is transversely spaced and longitudinally extended, and rigidly connected to ends of the transversely extending middle bar, and each of the pair of swing arms has a first end portion and an opposite, second end portion, wherein the first end portion of each swing arm is pivotally mounted to the frame structure; and the leg lifting actuator comprises a motor member, an outer tube extending from the motor member, an activation rod received in the outer tube, engaged with the motor member and configured to be telescopically movable relative to said outer tube according to a direction of motor rotation, wherein the motor member is pivotally connected to the frame structure, and the activation rod has a distal end portion pivotally connected to the middle bar of the leg lifting bracket, or wherein the motor member is pivotally connected to the middle bar of the leg lifting bracket, and the activation rod has a distal end portion pivotally connected to the frame structure.

12. The adjustable bed of claim 1, wherein the second end portion of at least one of the swing arms is equipped with a first lifting wheel and a second lifting wheel.

13. The adjustable bed of claim 1, wherein the frame structure comprises an upper rail, a lower rail, and a pair of side rails; wherein the upper rail and the lower rail are longitudinally spaced and transversely extended, and the pair of side rails is transversely spaced and longitudinally extended, and rigidly connected to the upper rail and the lower rail, such that the upper rail and the lower rail and the pair of side rails are co-planar in a rectangle form,
wherein the back lifting bracket of the back lifting assembly is pivotally connected to the pair of side rails of the frame structure, and the back lifting actuator of the back lifting assembly is pivotally connected between the back lifting bracket and the upper rail of the frame structure; and
wherein the leg lifting bracket of the leg lifting assembly is pivotally connected to the pair of side rails of the frame structure, and the leg lifting actuator of the leg lifting assembly is pivotally connected between the leg lifting bracket and the lower rail of the frame structure.

14. The adjustable bed of claim 1, wherein the frame structure comprises a back frame, and a leg frame,
wherein each of the back frame and the leg frame comprises an upper rail, a lower rail, and a pair of side rails; wherein the upper rail and the lower rail are longitudinally spaced and transversely extended, and the pair of side rails is transversely spaced and longitudinally extended, and rigidly connected to the upper rail and the lower rail, such that the upper rail and the lower rail and the pair of side rails are co-planar in a rectangle form;
wherein the back lifting bracket of the back lifting assembly is pivotally connected to the pair of side rails of the back frame, and the back lifting actuator of the back lifting assembly is pivotally connected between the back lifting bracket and the upper rail of the back frame; and wherein the leg lifting bracket of the leg lifting assembly is pivotally connected to the pair of side rails of the leg frame, and the leg lifting actuator of the leg lifting assembly is pivotally connected between the leg lifting bracket and the lower rail of the leg frame.

15. The adjustable bed of claim 14, wherein the frame structure further comprises a folding mechanism connecting the back frame and the leg frame such that the back frame and the leg frame are pivotably foldable to one another at the folding mechanism.

16. The adjustable bed of claim 1, wherein the plurality of platforms comprises a back platform movably disposed on the back lifting bracket;

an upper seat platform mounted on the frame structure and hinged with the back platform;

a lower seat platform mounted on the frame structure and being adjacent to the upper seat platform;

a thigh platform disposed on the leg lifting bracket and hinged with the lower seat platform; and a leg platform hinged with the thigh platform.

17. The adjustable bed of claim 16, wherein the leg lifting assembly further comprises a leg support member having a first end pivotally connected to the frame structure, and an opposite, second end pivotally connected to the leg platform.

18. An adjustable bed, comprising:

a frame structure;

a plurality of platforms disposed on the frame structure; and an adjustable assembly coupled with the frame structure and the plurality of platforms for operably adjusting one or more of the plurality of platforms in desired positions; and an aromatherapy system attached onto the one or more platforms for producing desired fragrance in a surrounding space of the adjustable bed so as to promote health and well-being of a user, wherein the aromatherapy system is an electric aromatherapy system comprising one or more aromatherapy devices;

wherein each aromatherapy device is configured to produce a fragrance when said aromatherapy device is turned on, wherein the fragrance is identical to or different from that produced by other aromatherapy device of the one or more aromatherapy devices; and wherein each aromatherapy device has one or more working modes, wherein the one or more working modes comprises a first working mode in which said aromatherapy device is turned on or turned off based on the user's instruction;

a second working mode in which said aromatherapy device is turned on for a first period of time, and then turned off; and a third working mode in which said aromatherapy device is turned on for a second period of time regularly in a third period of time.

\* \* \* \* \*